United States Patent [19]

Chandraratna

[11] Patent Number: 5,346,915
[45] Date of Patent: * Sep. 13, 1994

[54] CHROMANS AND THIOCHROMANS WITH PHENYLETHYNYL SUBSTITUENTS AT THE 7-POSITION HAVING RETINOLD-LIKE BIOLOGICAL ACTIVITY

[75] Inventor: Roshantha A. S. Chandraratna, El Toro, Calif.

[73] Assignee: Allergan, Inc., Irvine, Calif.

[*] Notice: The portion of the term of this patent subsequent to Dec. 25, 2007 has been disclaimed.

[21] Appl. No.: 1,009

[22] Filed: Jan. 6, 1993

Related U.S. Application Data

[63] Continuation of Ser. No. 655,524, Feb. 13, 1991, abandoned.

[51] Int. Cl.$^5$ .................... A61K 31/38; A61K 31/35; C07D 335/06; C07D 311/04
[52] U.S. Cl. .................... 514/432; 514/456; 549/23; 549/398
[58] Field of Search .................... 549/23, 407, 398; 514/432, 456

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 562/473 |
| 4,391,731 | 7/1983 | Boller et al. | 252/299.62 |
| 4,695,649 | 9/1987 | Magami et al. | 560/80 |
| 4,723,028 | 2/1988 | Shudo | 560/8 |
| 4,739,098 | 4/1988 | Chandraratna | 560/8 |
| 4,740,519 | 4/1988 | Shroot et al. | 514/443 |
| 4,810,804 | 3/1989 | Chandraratna | 549/23 |
| 4,826,969 | 5/1989 | Maignan et al. | 536/552 |
| 4,855,320 | 8/1989 | Chatterjee et al. | 514/473 |
| 4,895,868 | 1/1990 | Chandraratna | 549/23 |
| 4,980,369 | 12/1990 | Chandraratna | 514/432 |
| 4,992,468 | 2/1991 | Chandraratna | 514/532 |
| 5,006,550 | 4/1991 | Chandraratna | 549/405 |
| 5,013,744 | 5/1991 | Chandraratna | 514/435 |

(List continued on next page.)

FOREIGN PATENT DOCUMENTS

| | | |
|---|---|---|
| 0130795 | 1/1985 | European Pat. Off. ... C07D 311/58 |
| 176034A | 4/1986 | European Pat. Off. ... C07C 63/66 |
| 0284288 | 9/1988 | European Pat. Off. ... C07D 401/04 |
| 0350846 | 7/1989 | European Pat. Off. ... C07D 311/58 |
| 3708060 | 9/1987 | Fed. Rep. of Germany ... C07D 311/04 |

OTHER PUBLICATIONS

A. King et al A General Synthesis of Terminal and Internal Arylalkynes by the Palladium-Catalyzed Reaction of Alkynylzinc Reagents with Aryl Halides, *J. Org. Chem.* 43 No. 2, 1978 p. 358.

E. Negishi et al Conversion of Methyl Ketones into Terminal Acetylenes and (E)-Tri-substituted Olefins of Terpenoid Origin, *J. Org. Chem.* 45 No. 12, 1980 p. 2526.

(List continued on next page.)

*Primary Examiner*—Glennon H. Hollrah
*Assistant Examiner*—Mary C. Cebulak
*Attorney, Agent, or Firm*—Gabor L. Szekeres; Robert J. Baran; Martin A. Voet

[57] ABSTRACT

Novel compounds of the formula

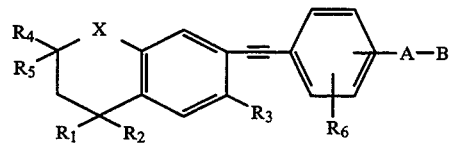

where X is S, O; $R_1$–$R_5$ are hydrogen or lower alkyl; $R_6$ is lower alkyl, lower alkenyl, lower cycloalkyl having 1 to 6 carbons, or halogen; A is lower branched chain alkyl having 2 to 6 carbons, cycloalkyl having 3 to 6 carbons, alkenyl having 2 to 6 carbons and 1 or 2 double bonds, alkynyl having 2 to 6 carbons and 1 or 2 triple bonds, $(CH_2)_n$ where n is 0–5; and B is hydrogen, COOH or a pharmaceutically acceptable salt thereof, $COOR_8$, $COONR_9R_{10}$, —$CH_2OH$, $CH_2OR_{11}$, $CH_2O$-$COR_{11}$, CHO, $CH(OR_{12})_2$, $CHOR_{13}O$, —COR'', $CR''(OR_{12})_2$, or $CR''OR_{13}O$, where R'' is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is lower alkyl, phenyl or lower alkylphenyl, $R_{12}$ is lower alkyl, $R_{13}$ is divalent alkyl radical of 2–5 carbons, have retinoic acid like activity.

30 Claims, No Drawings

U.S. PATENT DOCUMENTS

| | | | |
|---|---|---|---|
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/332 |
| 5,130,335 | 7/1992 | Chandraratna | 560/100 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |

OTHER PUBLICATIONS

Sporn et al. in *J. Amer. Acad. Derm.* 15:756–764 (1986).
S. Takahashi et al A Convenient Synthesis of Ethynylarenes and Diethynylarenes *Synthesis* 1980 p. 627–630.
Shudo et al. in *Chem. Phar. Bull.* 33:404–407 (1985).
Kagechika et al. in *J. Med. Chem.* 31:2182–2192 (1988).
M. Dawson et al., Chemistry and Biology of Synthetic Retinoids, published by CRC Press Inc., 1990, pp. 334–335, 354.
Meinc et al., Synthesis of 2,2′-Diacyl-1,1′-biaryls. Regiocontrolled Protection of . . . , *J. Org. Chem.,* No. 45, pp. 4720–4725, 1980.
L. Olson et al. A Dopamine Receptor Model and Its Application in the Design of a New Class of Rigid Pyrrolo[2,3-g]isoquinoline Antipsychotics, *American Chemical Society,* 1981, vol. 24, No. 9, pp. 1026–1031.
Williams et al, 6.2.3 Conformational Restriction, *Drug Discovery and Development,* 1987 The Humana Press, pp. 54–55.
Davis et al., V. Retinoid Structure–Biological Activity Relationships, Chemistry and Biology of Synthetic Retinoids, pp. 324–56 *J. Organomettalic Chem* 387 (1990) 381–390.

CHROMANS AND THIOCHROMANS WITH PHENYLETHYNYL SUBSTITUENTS AT THE 7-POSITION HAVING RETINOLD-LIKE BIOLOGICAL ACTIVITY

CROSS-REFERENCE TO RELATED APPLICATION

This application is a continuation of application Ser. No. 07/655,524 filed on Feb. 13, 1991, now abandoned.

BACKGROUND OF THE INVENTION

1. Field of the Invention

The present invention is directed to novel compounds which have retinoic acid-like biological activity. More specifically, the present invention relates to compounds having an ethynyl benzoic acid portion and a second portion which is a 2-and/or 4-substituted thiochromanyl, or chromanyl group. The acid function may also be converted to an alcohol, aldehyde or ketone, or derivatives thereof, or may be reduced to —CH$_3$.

2. Related Art

European Patent Application 176034A (published Apr. 2, 1986) discloses tetrahydronaphtalene compounds having an ethynylbenzoic group. U.S. Pat. No. 4,739,098 discloses compounds wherein three olefinic units from the acid-containing moiety of retinoic acid are replaced by an ethynylphenyl functionality. These compound have retinoic acid-like biological activity.

U.S. Pat. No. 4,810,804 (issued on Mar. 7, 1989) based on an application of the same inventor and assigned to the same assignee as the present application, discloses such disubstituted acetylene compounds wherein one of the substituents of the acetylene (ethyne) group is a substituted phenyl group, and the second substituent is a substituted or unsubstituted 6-chromanyl, 6-thiochromanyl or 6-tetrahydroquinolinyl group. The compounds disclosed and claimed in U.S. Pat. No. 4,810,804 have retinoic acid-like biological activity.

Several co-pending applications of the present inventor, which applications are assigned to the assignee of the present application, are directed to further types of disubstituted acetylene compounds wherein one substituent of the acetylene (ethyne) moiety is a substituted phenyl or a substituted heteroaryl group, and the other substituent is a substituted or unsubstituted 6-chromanyl, 6-thiochromanyl or 6-tetrahydroquinolinyl group. The disubstituted acetylene compounds described and claimed in the aforesaid co-pending applications have significant retinoic acid-like activity.

A published European patent application of the present applicant (Publication No. 0284288, published on Sep. 28, 1988) describes compounds having retinoic acid like activity which are 4,4 disubstituted chroman-6-yl, 4,4 disubstituted—thiochroman-6-yl acetylenes also substituted by a substituted heteroaryl group.

Retinoic acid-like activity has been generally recognized in the art to be associated with useful biological activity. Specifically, compounds having retinoic acid-like activity are useful as regulators of cell proliferation and differentiation, and particularly as agents for treating dermatoses, such as acne, Darier's disease, psoriasis, icthyosis, eczema, atopic dermatitis and epithelial cancers, for treating arthritic diseases and other immunological disorders (e.g. lupus erythematosus) for promoting wound healing, for treating dry eye syndrome and for reversing and preventing the effects of sun damage to skin.

With respect to the synthetic processes of the present invention which involve either the formation of an acetylenic (ethynyl) function in the compounds of the invention, or the coupling of the compounds of the invention which already have the ethynyl function with a halogen substituted phenyl group, the following articles comprise background information: A General Synthesis of Terminal and Internal Arylalkynes by the Palladium-Catalyzed Reaction of Alkynylzinc Reagents with Aryl Halides by Anthony O. King and Ei-ichi Negishi, *J. Org. Chem.* 43 1978 p 358; Conversion of Methyl Ketones into Terminal Acetylenes and (E)-Trisubstituted Olefins of Terpenoid Origin by Ei-ichi, Anthony O. King, and William L. Klima, *J. Org. Chem.* 45 1980 p.2526, and A Convenient Synthesis of Ethynylarenes and Diethynylarenes by S. Takahashi, Y. Kuroyama, K. Sonogashira, N. Hagihara, *Synthesis* 1980 p 627–630.

SUMMARY OF THE INVENTION

This invention covers compounds of Formula 1

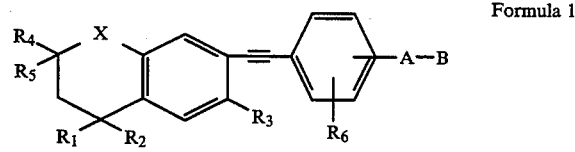

Formula 1 wherein X is S, O; R$_1$–R$_5$ are hydrogen or lower alkyl; R$_6$ is lower alkyl, lower alkenyl, lower cycloalkyl having 1 to 6 carbons, or halogen; A is lower branched chain alkyl having 2 to 6 carbons, cycloalkyl having 3 to 6 carbons, alkenyl having 2 to 6 carbons and 1 or 2 double bonds, alkynyl having 2 to 6 carbons and 1 or 2 triple bonds, (CH$_2$)$_n$ where n is 0–5; B is hydrogen, COOH or a pharmaceutically acceptable salt thereof, COOR$_8$, COONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR″, CR″(OR$_{12}$)$_2$, or CR″OR$_{13}$O, where R″ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5 to 10 carbons, or phenyl or lower alkylphenyl, R$_{11}$ is lower alkyl, phenyl or lower alkylphenyl, R$_{12}$ is lower alkyl, R$_{13}$ is divalent alkyl radical of 2–5 carbons.

In a second aspect, this invention relates to the use of the compounds of Formula 1 for treating dermatoses, such as ache, Darier's disease, psoriasis, icthyosis, eczema, atopic dermatitis and epithelial cancers. These compounds are also useful in the treatment of arthritic diseases and other immunological disorders (e.g. lupus erythematosus), in promoting wound healing, in treating dry eye syndrome and in reversing the effects of sun damage to skin.

This invention also relates to a pharmaceutical formulation comprising a compound of Formula 1 in admixture with a pharmaceutically acceptable excipient.

In another aspect, this invention relates to the process for making a compound of Formula 1 which process comprises reacting a compound of Formula 2 with a compound of Formula 3 in the presence of cuprous iodide and Pd(PQ$_3$)$_2$Cl$_2$ (Q is phenyl) or a similar complex

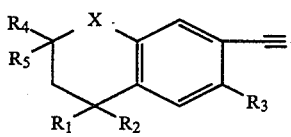

Formula 2

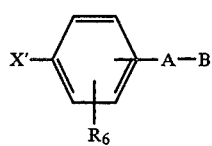

Formula 3 where R$_1$–R$_6$ are the same as described above, X' is a halogen, preferably I; and A is the same as defined above; and B is H, or a protected acid, alcohol, aldehyde or ketone, giving the corresponding compound of Formula 1; or to the process of making a compound of Formula 1 which consists of reacting a zinc salt of Formula 4 with a compound of Formula 3 in the presence of Pd(PQ$_3$)$_4$ (Q is phenyl) or a similar complex.

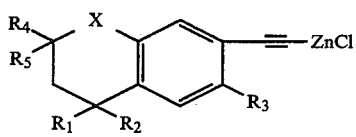

Formula 4 where R$_1$–R$_6$, and X, are the same as defined above, giving the corresponding compound of Formula 1; or homologating a compound of the Formula 5

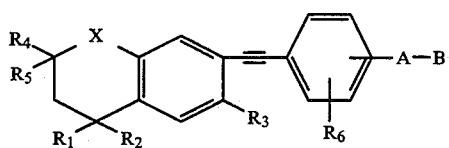

Formula 5 where n is 0–4 to give an acid of Formula 1; or
converting an acid of Formula 1 to a salt; or
forming an acid addition salt;
converting an acid of Formula 1 to an ester; or
converting an acid of Formula 1 to an amide; or
reducing an acid of Formula 1 to an alcohol or aldehyde; or
converting an alcohol of Formula 1 to an ether or ester; or
oxidizing an alcohol of Formula 1 to an aldehyde; or
converting an aldehyde of Formula 1 to an acetal; or
converting a ketone of Formula 1 to a ketal.

GENERAL EMBODIMENTS

Definitions

The term "ester" as used here refers to and covers any compound falling within the definition of that term as classically used in organic chemistry. Where B (of Formula 1) is —COOH, this term covers the products derived from treatment of this function with alcohols, preferably with aliphatic alcohols having 1–6 carbons. Where the ester is derived from compounds where B is —CH$_2$OH, this term covers compounds of the formula —CH$_2$OOCR where R is any substituted or unsubstituted aliphatic, aromatic or aliphatic-aromatic group, preferably with 1–6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Here, and where ever else used, lower alkyl means having 1–6 carbon atoms and includes straight as well as branched chain alkyl groups. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O— where R$_1$ is lower alkyl of 2–5 carbon atoms, straight chain or branched.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of this invention are those where the ethynyl group and the B group are attached to the 1 and 4 positions respectively of a benzene ring (i.e. where the phenyl moiety of the compound is para substituted) A is (CH$_2$)$_n$ and n is 0; and B is —COOH, an alkali metal salt or organic amine salt, or a lower alkyl ester thereof, or —CH$_2$OH and the lower alkyl esters and ethers thereof, (formed with a lower alkanol) or —CHO and acetal derivatives thereof. The more preferred compounds shown in Formula 6 are:
  ethyl 4-(4,4-dimethyl-7-thiochromanyl)-ethynyl-benzoate (Compound 1, X=S, R$_3$=H, R$_4$=H, R$_5$=H, R"=C$_2$H$_5$);
  4-[(4-4-dimethyl-7-thiochromanyl)-ethynyl]-benzoic acid (Compound 2, X=S, R$_3$=H, R$_4$=H, R$_5$=H, R"=H);

ethyl 4-(2,2,4,4-tetramethyl-7-thiochromanyl)-ethynylbenzoate (Compound 3, X=S, $R_3$=H, $R_4$=$CH_3$, $R_5$=$CH_3$, R''=$C_2H_5$);

ethyl-4-(2,2,4,4-tetramethyl-7-chromanyl)-ethynyl-benzoate (Compound 4, X=O, $R_3$=H, $R_4$=$CH_3$, $R_5$=$CH_3$, R''=$C_2H_5$).

4-(2,2,4,4-tetramethyl-7-thiochromanyl)-ethynyl benzoic acid (Compound 49, X=S, $R_3$=H, $R_4$=$CH_3$, $R_5$=$CH_3$, R''=H).

4-(2,2,4,4-tetramethyl-7-chromanyl)-ethynyl benzoic acid (Compound 50, X=O, $R_3$=H, $R_4$=$CH_3$, $R_5$=$CH_3$, R''=H).

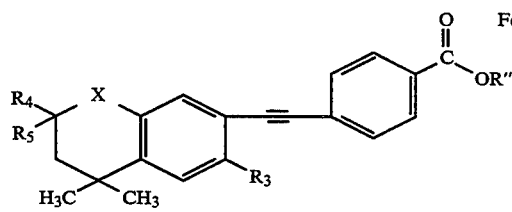

Formula 6

The compounds of this invention may be administered systemically or topically, depending on such considerations as the condition to be treated, need for site-specific treatment, quantity of drug to be administered, and similar considerations.

In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

The retionic acid like activity of these compounds was confirmed through the classic measure of retionic acid activity involving the effects of retionic acid on ornithine decarboxylase. The original work on the correlation between retinoic acid and decrease in cell proliferation was done by Verma & Boutwell, Cancer Research, 1977, 37, 2196-2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-0-tetradecanoylphorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in Cancer Res., 35: 1662-1670, 1975.

By way of example of retinoic acid-like activity it is noted that in the assay conducted essentially in accordance with the method of Verma & Boutwell, ibid, the following examples of the preferred compounds of the present invention (Compounds 1, 2, 3 and 4) attained an 80% inhibition of TPA induced ODC activity at the following concentrations ($IC_{80}$):

| Compound | $IC_{80}$ conc (nmols) |
|---|---|
| 1 | 0.81 |
| 2 | 1.54 |
| 3 | 1.23 |
| 4 | 0.35 |

SPECIFIC EMBODIMENTS

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

Compounds of Formula 1 where X is —S— and $R_4$ and $R_5$ are hydrogen or lower alkyl, are prepared as per Reaction Scheme 1

Reaction Scheme 1

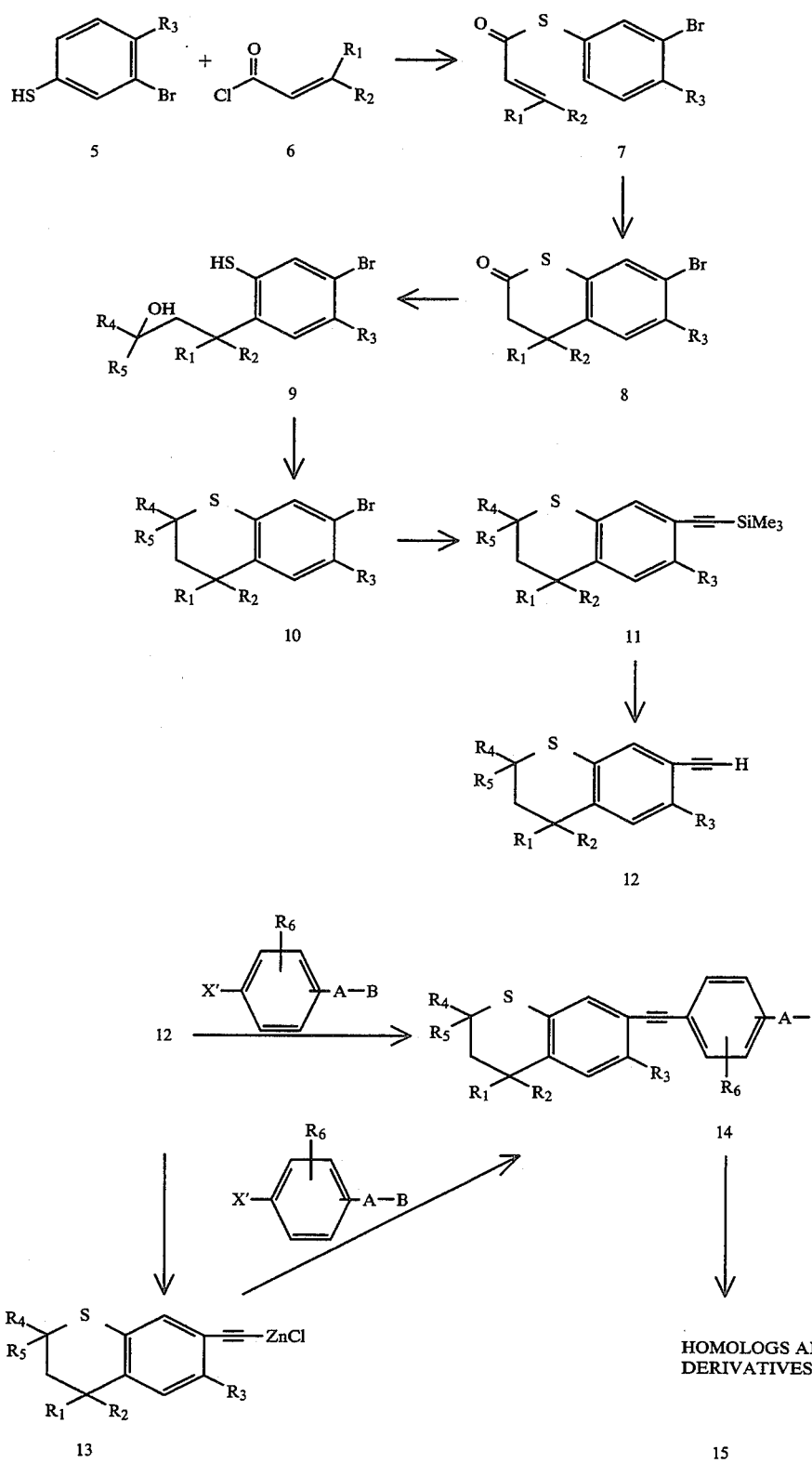

In Reaction Scheme 1, $R_1$–$R_5$ are hydrogen or a lower alkyl group, $R_6$ is defined as above in connection with Formula 1, A is lower branched chain alkyl having 2 to 6 carbons, cycloalkyl having 3 to 6 carbons, alkenyl having 2 to 6 carbons and 1 or 2 double bonds, alkynyl having 2 to 6 carbons and 1 or 2 triple bonds, $(CH_2)_n$ where n is 0–5 and B is H, or a protected acid, alcohol, aldehyde or ketone. X′ is Cl, Br or I when n is 0 but preferably is Br or I when n is 1–5.

Compounds of Formula 1 where X is oxygen and $R_4$ and $R_5$ are hydrogen or lower alkyl, are prepared as per Reaction Scheme 2.

Reaction Scheme 2

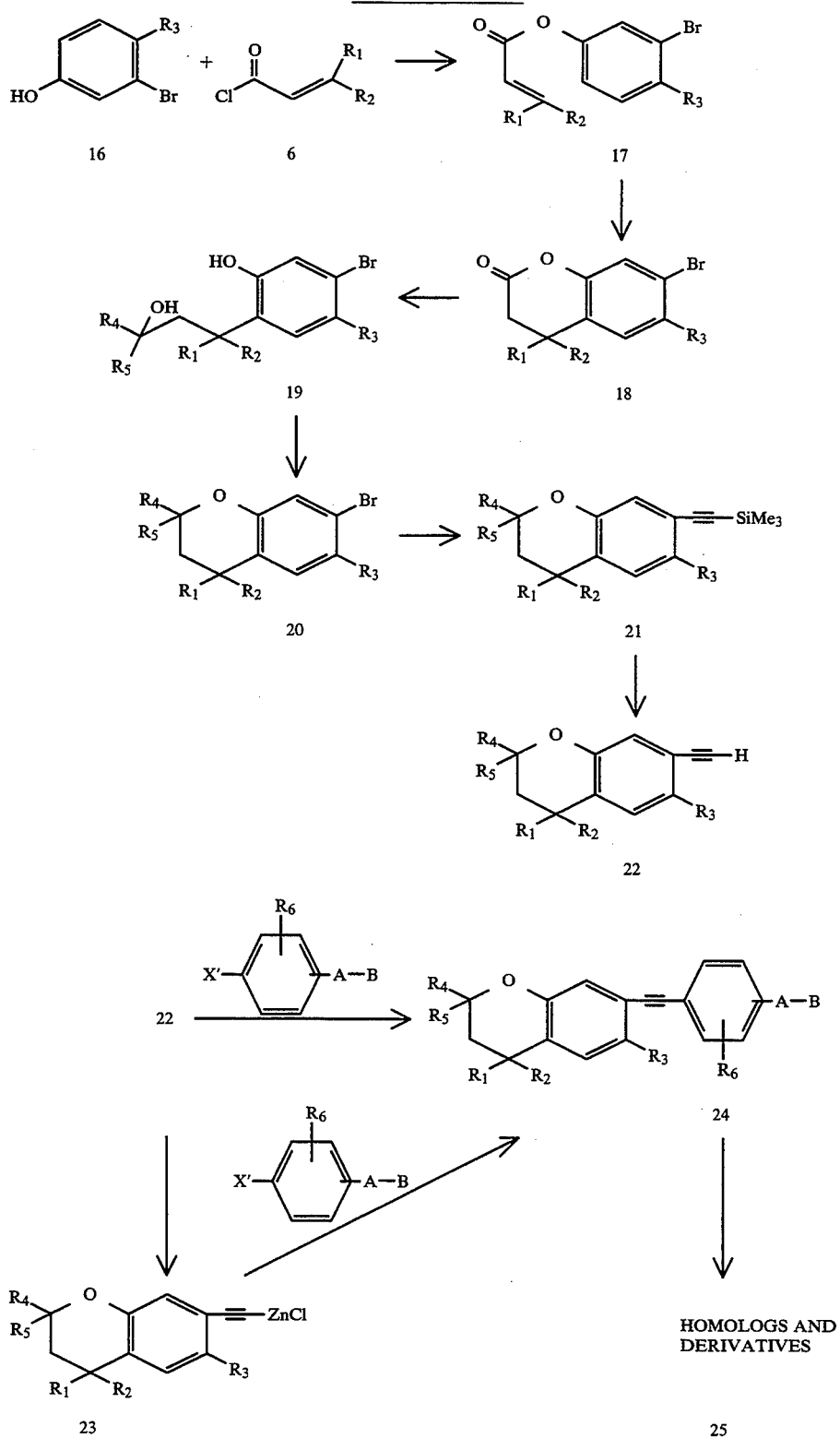

In Reaction Scheme 2 the definitions of $R_1$–$R_6$, A, B and X' are the same as in Reaction Scheme 1.

A general description of the synthetic steps outlined in Reaction Schemes 1 and 2 is as follows.

In Reaction Scheme 1 the 3-bromo-thiophenol (Compound 5) is acylated with an acylating agent, such as an acid chloride (Compound 6) derived from an appropriately substituted acrylic acid. The acylation is conducted in an inert solvent (such as tetrahydrofuran) in the presence of strong base (for example sodium hydrdride). The resulting thioester (Compound 7) which contains the olefinic bond of the acrylic acid moiety is ring closed in the presence of a Friedel Crafts type catalyst (such as aluminum chloride) by stirring in a suitable solvent such as methylene chloride. The resulting 2-oxo-7-bromothiochroman (Compound 8) is usually isolated in crystalline form.

The $R_4$ and/or $R_5$ substituents are introduced by treating the 2-oxo-7-bromo-thiochroman (Compound 8) with a Grignard reagent in the presence of $CeCl_3$, bearing the alkyl substituents $R_4$ and $R_5$ (such as methylmagnesium bromide when $R_4$ and $R_5$ are methyl). When the Grignard reagent (such as methylmagnesium bromide) is in excess, the thiochroman ring is opened and the tertiary alcohol derivative of the 3-bromo thiophenol (Compound 9) is formed.

Ring closure of the thiophenol derivative (Compound 9) which has the desired $R_1$, $R_2$, $R_3$, $R_4$ and $R_5$ substituents, is affected by heating in acidic conditions, preferably by heating Compound 9 in aqueous acid. The resulting 7-bromothiochroman which bears the desired alkyl (or hydrogen) substituents, $R_1$, $R_2$, $R_3$, $R_4$ and $R_5$ is shown as Compound 10 in Reaction Scheme 1.

To introduce the acetylene (ethyne) portion into the molecule, the substituted 7-bromothiochroman (Compound 10) is reacted with trimethylsilylacetylene in the presence of cuprous iodide and a suitable catalyst, typically having the formula $Pd(PQ_3)_2Cl_2$ (Q is phenyl). The reaction is typically conducted in the presence of bis(triphenylphosphine) palladium (II) chloride catalyst and an acid acceptor (such as triethylamine) under an inert gas (argon) atmosphere, by heating in a sealed tube. The resulting 7-trimethylsilylethynylthiochroman is shown as Compound 11 in Reaction Scheme 1.

As is shown on Reaction Scheme 1, the trimethylsilyl moiety is removed from the 7-trimethylsilylethynyl-thiochroman (Compound 11) in the next synthetic step, to provide the ring substituted 7-ethynyl-thiochroman derivative (Compound 12). The latter reaction is conducted under basic conditions, preferably under an inert gas atmosphere.

In order to introduce the phenyl or substituted phenyl substituent on the acetylene (ethyne) portion of Compound 12, Compound 12 is coupled with the reagent X'—Q—A—B (Formula 3, Q is a di- or multi-substituted phenyl residue) where the symbols A, X' and B have the same meaning as defined in connection with Formula 3. In other words, the phenyl or substituted phenyl substituent is introduced into the 7-ethynyl-thiochroman (Compound 12) by reacting the latter with a halogen substituted phenyl compound (Formula 3) in which the benzene nucleus either has the desired substituent [A-B] or wherein the actual substituent A-B can be readily converted to the desired substituent by means of organic reactions well known in the art.

Coupling of the 7-ethynyl-thiochroman (Compound 12) with the reagent X'—Q—A—B is affected directly in the presence of cuprous iodide, a suitable catalyst, typically of the formula $Pd(PQ_3)_2Cl_2$ and an acid acceptor, such as triethylamine, by heating in a sealed tube under an inert gas (argon) atmosphere.

The resulting disubstituted acetylene compound (Compound 14) may be the target compound made in accordance with the invention, or maybe readily converted into the target compound by such steps as salt formation, esterification, deesterification, homologation, amide formation and the like. These steps are further discussed below.

Compound 14 may also be obtained by first converting the 7-ethynyl-thiochroman derivative (Compound 12) into a corresponding metal salt, such as a zinc salt, (Compound 13) and thereafter coupling the salt (Compound 13) with the reagent X'—Q—A—B (Formula 3 Q is phenyl or substituted phenyl residue) in the presence of a catalyst having the formula $Pd(PQ_3)_4$ (Q is phenyl), or similar complex.

Derivatization of Compound 14 is indicated in Reaction Scheme 1 as conversion to "homologs and derivatives" Compounds 15.

More specifically with respect to either derivatization or deblocking of protected functionalities in Compound 14, or with respect to the preparation of phenyl derivatives of the formula X'—Q—A—B, (which after coupling either directly yield the compounds of the invention, or are readily converted into them) the following is noted.

Where a protected phenyl derivative is needed to couple with the compounds of Formula 2 (Compounds 12 in Reaction Scheme 1), such may be prepared from their corresponding acids, alcohols, ketones or aldehydes. These starting materials, the protected acids, alcohols, aldehydes or ketones, are all available from chemical manufacturers or can be prepared by published methods. Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before effecting a coupling reaction, where such compounds are not available from a commercial source, the phenyl derivatives where B is —COOH are subjected to homologation by successive treatment under Arndt-Eistert conditions or other homologation procedures. Alternatively, phenyl derivatives where B is different from COOH, may also be homologated by appropriate procedures. The homologated acids can then be esterified by the general procedure outlined in the preceding paragraph.

An alternative means for making compounds where A is $(CH_2)_n$ n is 1–5 is to subject the compounds of Formula 1, where B is an acid or other function, to homologation, using the Arndt-Eistert method referred to above, or other homologation procedures.

Compounds of Formula 1 where A is an alkenyl group having one or more double bonds can be made for example, by having the requisite number of double bonds incorporated into the intermediate of Formula 3; that is by using for the intermediate of Formula 3 an unsaturated aromatic compound bearing the X' leaving group (preferably halogen) in the phenyl nucleus. 4-Bromo or 4-iodo-cinnamic acid ethyl ester serve as concrete examples. Generally speaking, the compounds of Formula 3 where A is an unsaturated carbon chain can be obtained by synthetic schemes well known to the practicing organic chemist; for example by Wittig and like reactions, or by introduction of a double bond by elimination of halogen from an alpha-halo-phenylalkyl-carboxylic acid, ester or like carboxaldehyde. Compound of Formula 1 where the A group has a triple (acetylenic) bond can be made by using the corresponding intermediate of Formula 3. Such intermediate can be obtained by reactions well known in the art, for example, by reaction of a corresponding phenyl-methyl ketone with strong base, such as lithium diisopuopyl amide.

The acids and salts derived from Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about $-10$ degrees and $+10$ degrees C. The last mentioned solution is then stirred at the reduced temperature for 1-4 hours, preferably 2 hours. Solvent removal provides a residue which is taken up in an inert inorganic solvent such as benzene, cooled to about 0 degrees C. and treated with concentrated ammonium hydroxide. The resulting mixture is stirred at a reduced temperature for 1-4 hours. The product is recovered by conventional means.

Alcohols are made by converting the corresponding acids to the acid chloride with thionyl chloride or other means (J. March "Advanced Organic Chemistry" 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexlcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds where B is H can be prepared from the corresponding halogenated benzene compounds, preferably where the halogen is I.

With reference to Reaction Scheme 2, 3-bromophenol, or a 3-bromophenol substituted in the 4-(para) position by an alkyl substituent ($R_3$) (Compound 16) is acylated with an acylating agent, such as an acid chloride (Compound 6) derived from an appropriately substituted acrylic acid. In Reaction Scheme 2, just as in Reaction Scheme 1, the $R_1$ and $R_2$ substituents of the target compounds are introduced through this acrylic acid derivative (Compound 6). The acylation with the acid chloride (Compound 6) is preferably conducted in the presence of a strong base (e.g. sodium hydride) in an inert solvent (such as tetrahydrofuran). The resulting substituted phenyl-acrylate is shown in Reaction Scheme 2 as Compound 17.

The substituted phenyl-acrylate 17 is ring closed under Friedel Crafts type reaction conditions ($AlCl_3$ catalyst, in an inert solvent, such as methylene chloride) to provide the 2-oxo-7-bromo-chroman compound (Compound 18) which bears, in the 4-position, the $R_1$ and $R_2$ substituents and in the 6-position the $R_3$ substituent (as applicable). Just like the analogous 2-oxo-thiochroman (Compound 8) in Reaction Scheme 1, the 2-oxo-chroman 18 of Reaction Scheme 2 is treated with a Grignard reagent to introduce the $R_4$ and $R_5$ substituents. When $R_4$ and $R_5$ are methyl, the Grignard reagent is preferably methylmagnesium chloride (dissolved in tetrahydrofuran, THF). A solution of Compound 18 in a suitable solvent, for example in dry diethylether is added to this Grignard reagent. The resulting phenol containing a tertiary alcohol side chain, (that is a molecule in which the chroman ring had been opened) is shown in Reaction Scheme 2 as Compound 19.

Compound 19 which already has the desired $R_1$, $R_2$, $R_3$, $R_4$ and $R_5$ substituents, is ring closed under acidic conditions, (e.g. by heating in aqueous sulfuric acid) to provide the chroman derivative (Compound 20). To introduce the acetylene (ethyne) portion into the molecule, the substituted 7-bromo chroman (Compound 20) is reacted with trimethylsilyl acetylene in the presence of cuprous iodide and a suitable catalyst, typically having the formula $Pd(PQ_3)_2 Cl_2$ (Q is phenyl), as defined for the 7-bromo-thiochroman compound in Reaction Scheme 1. The resulting 7-trimethylsilyl-ethynyl-chroman is shown as Compound 21 in Reaction Scheme 2.

In Reaction Scheme 2, just as in Reaction Scheme 1, the trimethylsilyl moiety is removed from the 7-trimethylsilylethynyl-chroman (Compound 21) under basic conditions, to provide the ring substituted 7-ethynyl-chroman derivative (Compound 22).

Referring still to Reaction Scheme 2, the 7-ethynyl-chroman derivative (Compound 22) may be converted into the target compounds of the invention in synthetic steps which are analogous to the conversion of 7-ethynyl-thiochromans (Compound 12) into the corresponding target thiochroman derivatives (See Reaction Scheme 1). Briefly, Compound 22 is preferably heated with a reagent X'—Q—A—B (Formula 3, Q is phenyl or substituted phenyl residue) in the presence of cuprous iodide, a suitable catalyst, typically of the formula $Pd(PQ_3)_2 Cl_2$ (Q is phenyl or the like) and an acid acceptor, such as triethylamine. This coupling reaction, yields the target chroman compounds, (Compound 24) or such derivatives which are readily converted into the target compounds by protection, deprotection, esterification, homologation etc., as is discussed in connection with Reaction Scheme 1. The homologs are indicated, as a group, as Compound 25 in Reaction Scheme 2.

$R_4$ and $R_5$ with one of $R_4$ or $R_5$ being hydrogen, is shown as Compound 10.

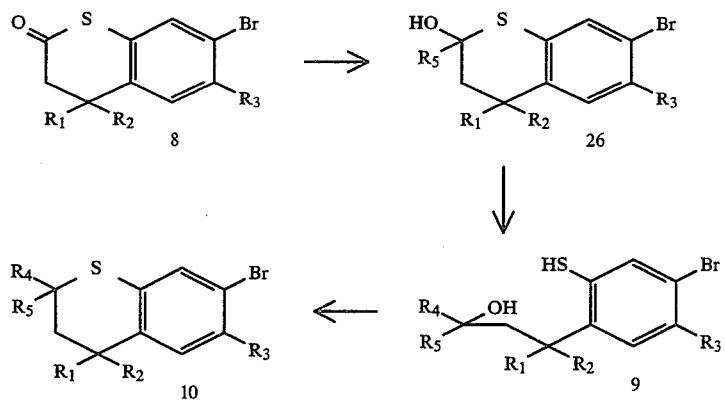

Reaction Scheme 4

Alternatively, the 7-ethynyl-chroman compounds (Compound 22) may first be converted to the corresponding metal (zinc) salt (Compound 23) and thereafter coupled with the reagent X'—Q—A—B (Formula 3, Q is phenyl or substituted phenyl residue) under conditions which are similar to the conditions described in Reaction Scheme 1 for coupling of Compounds 13 with the same reagent.

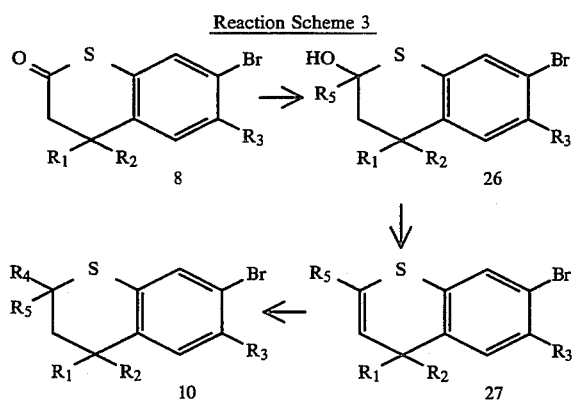

Reaction Scheme 3

Referring to Reaction Scheme 3, the substituted 7-bromothiochroman (Compound 10), where one of the $R_4$ or $R_5$ substituents is alkyl and the other is hydrogen, can be made by treating the 2-oxo-7-bromo-thiochroman (Compound 8) with a Grignard reagent. As in Reaction Scheme 1 the 2-oxo-thiochroman (Compound 8) is subjected to an excess of Grignard reagent, bearing the alkyl substituents $R_4$ or $R_5$ (such as methylmagnesium bromide when $R_4$ or $R_5$ is methyl). However, the reaction temperature is controlled and maintained at a relatively low temperature (such as −14 degrees C.) and the duration of the reaction is kept relatively short (0.5 hours). A hemiacetal derivative of 3-bromothiophenol (Compound 26) is formed in this controlled Grignard reaction, as shown in Reaction Scheme 3. Compound 26 is converted by heating in acidic conditions, preferably with aqueous acid, to the unsaturated derivative (Compound 27). Compound 27 is reduced by hydrogenation in the presence of palladium sulfide-on-carbon catalyst at increased pressure (approximately 30 psi). The resulting 7-bromo-thiochroman which bears the desired hydrogen and alkyl substituents $R_1$, $R_2$, $R_3$, To obtain the 7-bromothio chroman (Compound 10), (Reaction Scheme 4) where the $R_4$ and $R_5$ substituents both are alkyl but not identical with one another, the hemiacetal derivative (Compound 26) is treated with a different Grignard reagent than previously used, as shown in Scheme 4. In this Grignard reaction the thiochroman ring is opened and the tertiary alcohol derivative of 3-bromo-thiophenol (Compound 9), is formed. Ring closure of the thiophenol derivative (Compound 9) which has the desired $R_1$, $R_2$, $R_3$, $R_4$ and $R_5$ substituents, is affected by heating in acidic conditions, preferably by heating with aqueous acid. The resulting 7-bromo thiochroman which bears the desired alkyl and hydrogen substituents $R_1$, $R_2$, $R_3$, $R_4$ and $R_5$ is shown as Compound 10.

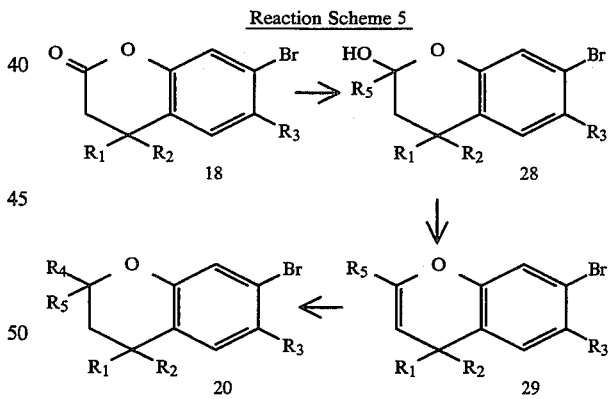

Reaction Scheme 5

In Reaction Scheme 5, just as in Reaction Scheme 3, one of the $R_4$ or $R_5$ substituents is alkyl and the other is hydrogen. Just like the analogous 2-oxo-thiochroman (Compound 8) in Reaction Scheme 3, the 2-oxochroman (Compound 18) of Reaction Scheme 5 is treated with a Grignard reagent to introduce the $R_4$ and $R_5$ substituents. With controlled reaction temperature and time, the resulting hemiacetal derivative can be isolated as Compound 28, as shown in Reaction Scheme 5. Under acidic conditions, (e.g. by heating in aqueous acid) the hemiacetal (Compound 28) is cyclized to form the corresponding unsaturated derivative (Compound 29). The unsaturated derivative can then be reduced using the same conditions as described in connection with Reaction Scheme 3 for the reduction of Compound 26, or by a more general reducing procedure. The resulting chroman derivative is shown as Compound 20 in Reaction Scheme 5.

Thus, with reference to Reaction Scheme 7, the 3-bromothiophenol (Compound 5) (which maybe alkyl substituted in the 4-position) is alkylated with Com-

Reaction Scheme 6

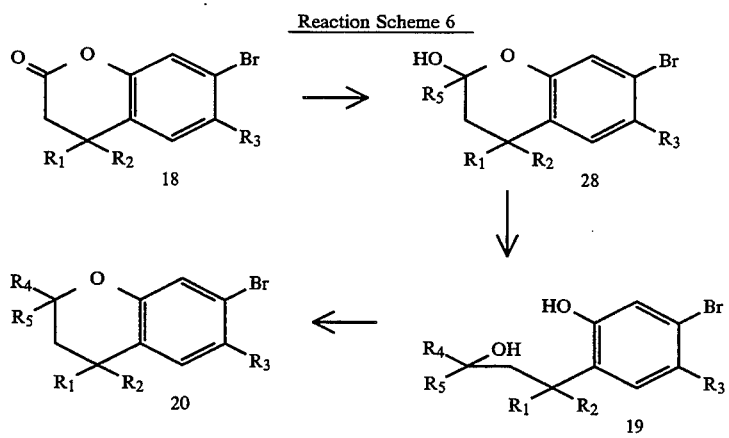

Referring to Reaction Scheme 6, in Compound 20 of that scheme the $R_4$ and $R_5$ substituents are alkyl but are not identical. The $R_4$ and $R_5$ alkyl substituents are introduced by treating Compound 28 with a different Grignard reagent than previously used, to form the tertiary alcohol (Compound 19). The tertiary alcohol (Compound 19) which already has the desired $R_1$, $R_2$, $R_3$, $R_4$ and $R_5$ substituents, is ring closed under acidic conditions, as described above, to provide the chroman derivative (Compound 20).

In order to obtain the final acetylenic products where one of the $R_4$ or $R_5$ substituent is alkyl and the other is hydrogen, or where the $R_4$ and $R_5$ substituents are alkyl but not identical to one another, Compounds 10 and 20 are subjected to substantially the same reaction procedures as outlined in Reaction Scheme 1 and Reaction Scheme 2.

With reference to the compounds of Formula 1, Reaction Scheme 7 illustrates an example of their synthesis when X=S and $R_4$ and $R_5$ are both hydrogen.

pound 30. The resulting 3-bromo phenyl sulfides (Compound 31) are ring closed under Friedel Crafts (or like) conditions by refluxing in an inert solvent such as benzene or toluene, in the presence of phosphorus pentoxide and phosphoric acid. The resulting thiochroman (Compound 10) made in accordance with Reaction Scheme 7 has $R_4$ and $R_5$ as hydrogen, and preferably in accordance with this reaction scheme, $R_1$ and $R_2$ are methyl and $R_3$ is hydrogen.

To introduce the acetylene (ethyne) portion into the molecule, the substituted 7-bromothiochromane (Compound 10) is reacted with trimethylsilyl-acetylene in the presence of cuprous iodide and a suitable catalyst, typically having the formula Pd(PQ$_3$)$_2$Cl$_2$ (Q is phenyl). The reaction is typically conducted in the presence of bis(triphenylphosphine) palladium (II) chloride catalyst, an acid acceptor, (such as triethylamine) under an inert gas (argon) atmosphere, by heating in a sealed tube. The resulting 7-trimethylsilylethynylthiochroman, is shown as Compound 11 in Reaction Scheme 7.

Reaction Scheme 7

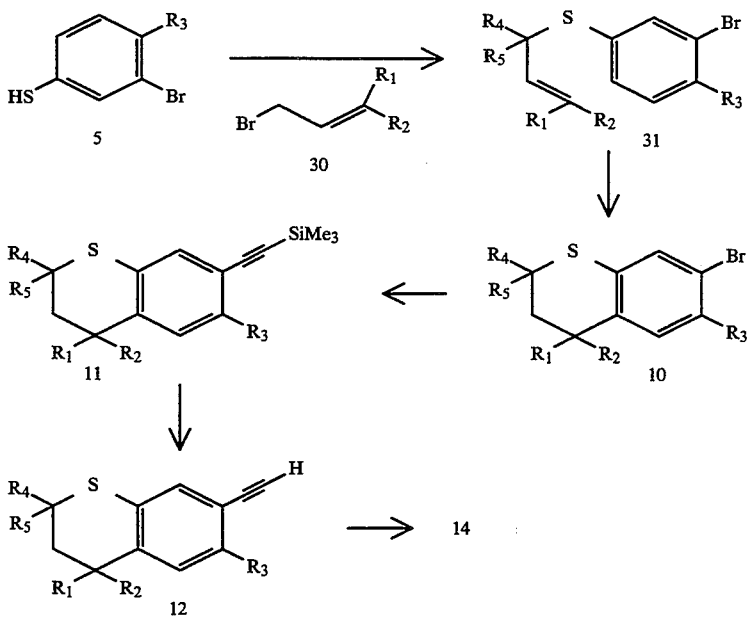

As is further shown on Reaction Scheme 7, the trimethylsilyl moiety is removed from the 7-trimethylsilylethynyl-thiochroman (Compound 11) in the next synthetic step, to provide the ring substituted 7-ethynyl-thiochroman derivative (Compound 12). The latter reaction is conducted under basic conditions, preferably under an inert gas atmosphere.

The 7-ethynyl-thiochroman (Compound 12) can be utilized directly in the coupling reaction set forth in Reaction Scheme 1, or prior to coupling can be converted to the corresponding ZnCl salt, as is described above.

Turning to compounds of Formula 1 where X=O and where $R_4$ and $R_5$ are H, (that is turning to chromans substituted in the 4, and possibly in the 6 position) the compounds can be made as indicated in Reaction Scheme 8.

under basic conditions, preferably under an inert gas atmosphere.

The 7-ethynyl-thiochroman (Compound 22) can be utilized directly in the coupling reaction as described for Reaction Scheme 2, or prior to coupling can be converted to the corresponding ZnCl salt as is described above.

SPECIFIC EXAMPLES

S-(3-Bromophenyl) 3,3-dimethyl-thio acrylate (Compound 33)

To an ice-bath cooled solution of 4.5 g (112.5 mmol) of sodium hydride (60% suspension in mineral oil) in 50 ml of dry THF was added slowly under argon a solution of 20 g (105.8 mmol) of 3-bromothiophenol in 80 ml of dry THF. The mixture was stirred at 0° C. for 30 minutes and then treated with a solution of 14 g (118

Reaction Scheme 8

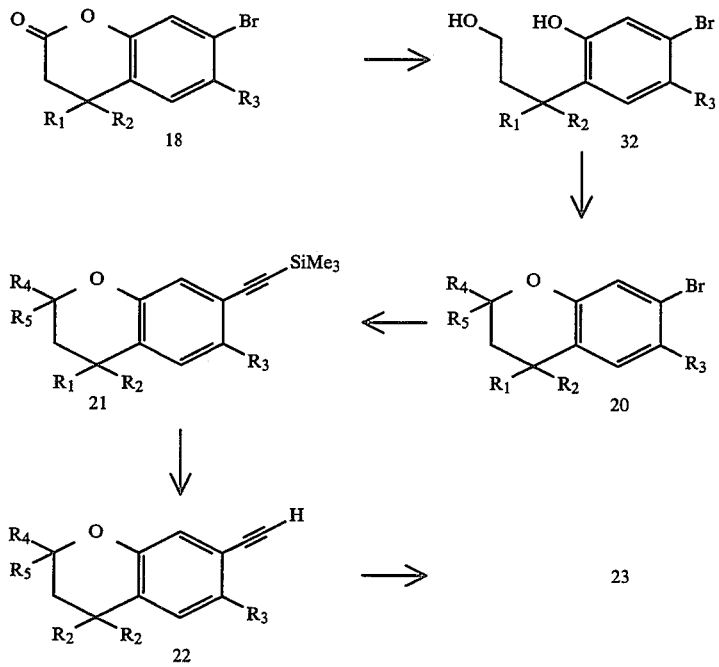

In Reaction Scheme 8 $R_1$ and $R_2$ are hydrogen or lower alkyl having 1 to 6 carbons, and $R_3$ is defined as above in connection with Formula 1.

The 2-oxo-chroman (Compound 18) of Reaction Scheme 2 is reduced with lithium aluminum hydride (or by a similar reducing agent) to provide the diol (Compound 32). The primary hydroxyl group of Compound 32 is selectively mesylated over the phenolic hydroxyl, followed by intramolecular displacement of the mesylate group under basic conditions, to give a 7-bromo-chroman derivative (Compound 20) which bears the desired alkyl substituents at $R_1$ and $R_2$ and where $R_4$ and $R_5$ are both hydrogen. The acetylenic (ethyne) function is introduced into the 4,4 disubstituted (and optionally 6-substituted) chroman Compound 20 in a sequence of reaction steps which are described in Reaction Scheme 7 in connection with the analogous thiochroman compounds.

As is further shown on Reaction Scheme 8 and in analogy to the reaction sequence shown on Reaction Scheme 7, the trimethylsilyl moiety is removed from 7-trimethylsilyl-ethynyl-thiochroman (Compound 21)

mmol) of dimethylacryloyl chloride in 30 ml of dry THF. The reaction mixture was allowed to stir at room temperature for 24 hours. The reaction mixture was poured onto 300 ml of water containing 5 ml of glacial acetic acid and the organic layer was separated. The aqueous layer was extracted with 2×200 ml ether. The organic extracts were combined and washed with 100 ml of water and 100 ml of saturated NaCl solution and then dried (MgSO$_4$). The solvent was removed in vacuo and the residue was kugelrohr distilled to give the title compound as a pale yellow oil.

PMR (CDCl$_3$); & 1.90 (3H, s), 2.14 (3H, s), 6.04 (1H, s), 7.26 (1H, t, J~7.8 Hz), 7.36 (1H, d, J~4 Hz), 7.5 (1H, dd, J~7.8 Hz, J~1.7 Hz), 7.59 (1H, d, J~1.7 Hz)

4,4 Dimethyl-7-bromo-2-oxo-thiochroman (Compound 34)

To a stirred, ice cooled suspension of 20 g (150 mmol) of aluminum chloride in 250 ml of methylene chloride was added a solution of 17 g (89.5 mmol) of S-(3-bromopenyl) 3-3 dimethylthio acrylate (Compound 33) in 100 ml of methylene chloride. The mixture was stirred at room temperature for 24 hours and then poured nto 200 ml of an ice and brine mixture. The organic layer was separated and the aqueous layer was extracted with 150 ml of ether. The organic extracts were combined arid then washed with water and saturated NaCl solution and dried (MgSO4). The solvent was removed in vacuo and the residue purified by flash column chromatography (silica; 2% ethyl acetate, hexanes) to give the title compound as a white solid.

PMR (CDCl3); & 1.38 (6H, s), 2.65 (2H, s) 7.33 (3H, s).

5-Bromo-2-(1,1,3-trimethyl-3 hydroxy butyl)-thiophenol (Compound 35)

To 132 g (354.3 mmol) of Cerium chloride (dried under vacuum at 135° C. for 2 days) was added 200 ml of dry THF, and the suspension was stirred at room temperature for 20 hours. The reaction mixture was then cooled to 0° C. and treated with 103 ml (309 mmol) of a 3.0M solution of methyl magnesium chloride in THF. The mixture was stirred at room temperature for 4 hours, cooled to 0° C., and treated with a solution of 9.6 g (35.4 mmol) of 4-4 dimethyl-7-bromo-2-oxo-thiochroman (Compound 34) in 60 ml of dry THF. The reaction mixture was allowed to stir at room temperature for 18 hours and then poured into 200 ml of ice containing 2 ml of sulfuric acid. The mixture was extracted with 500 ml of ether. The ether extracts were combined and washed with 300 ml of water and 300 ml of saturated NaCl solution and then dried (MgSO4). The solvent was removed in vacuo to give the title compound as a pale yellow oil.

PMR (CDCl3); & 1.08 (6H, s), 1.54 (6H, s), 2.31 (2H, s), 7.24 (1H, dd, J~8.5 Hz, J~2 Hz), 7.30 (1H, d, J~8.5 Hz) 7.34, (1H, d, J~2 Hz).

2,2,4,4 Tetramethyl-7-bromo-thiochroman (Compound 36)

A mixture of 10 g (33 mmol) of 5-bromo-2-(1,1,3-trimethyl-3-hydroxybutyl) thiophenol (Compound 35) and 100 ml of 20 percent aqueous sulfuric acid was heated at reflux for 48 hours. The mixture was cooled to room temperature and extracted with 2×50 ml of ether. The ether extracts were combined and washed with 25 ml of saturated sodium bicarbonate solution and 25 ml of saturated NaCl solution and dried (MgSO4). The solvent was removed in vacuo and the residue purified by flash column chromatography (silica: 2% ethyl acetate in hexanes) followed by kugelrohr distillation to give the title compound as a clear oil.

PMR (CDCl3); & 1.810 (6H, s), 1.282 (6H, s), 1.234 (2H, s), 7.047 (1H, dd, J~2 Hz, J~8.8 Hz) 7.114 (1H, d J~8.8 Hz) 7.16 (1H, d, J~2 Hz).

2,2,4,4 Tetramethyl-7-trimethylsilyl-ethynyl-thiochroman (Compound 37)

A solution of 3 g (10.5 mmol) of 2,2,4,4 tetramethyl-7-bromo-thiochroman (Compound 36) and 5.16 g (52.6 mmol) of trimethylsilylacetylene in 5 ml of triethylamine was placed in a heavy walled glass tube and degassed under nitrogen. The mixture was then treated, under nitrogen, with 184 mg (0.966 mmol) of cuprous iodide and 368 mg (0.524 mmol) of bis (triphenylphosphine) palladium (II) chloride, the reaction mixture was degassed again and placed under nitrogen and the tube was sealed. The mixture was heated at 60° C. for 24 hours, cooled to room temperature, and then filtered through celite. The solvent was removed in vacuo and the residue purified by flash column chromatography (silica; 100% hexanes) to give the title compound as a pale yellow solid.

PMR (CDCl3); & 0.22 (9H, s), 1.35 (6H, s), 1.38 (6H, s), 1.93 (2H, s), 7.16 (1H, dd, J~8.1 Hz, J~1.74 Hz), 7.24 (1H, d, J~1.74 Hz) 7.30 (1H, J~8.1 Hz)

2,2,4,4-Tetramethyl-7-ethynyl-thiochroman (Compound 38)

To a solution of 1.04 g (3.4 mmole) of 2,2,4,4 tetramethlyl-7-trimethylsilylethynyl thiochroman (Compound 37) in 3 ml of isopropanol was added 5 ml of ethanolic KOH solution. The reaction mixture was stirred at room temperature for 24 hours and the alcohol was then removed in vacuo. The residue was extracted with ether (20 ml) and the combined ether layers were washed with water (15 ml) and saturated NaCl solution (20 ml) and dried (MgSO4). The solvent was removed in vacuo and the residue purified by kugelhohr distillation to give the title compound as a clear oil.

PMR (CDCl3); & 1.38 (6H, s), 1.42 (6H, s), 1.95 (2H, s), 3.02 (1H, s), 7.20 (1H, dd, J~8.1 Hz, 2.1 Hz), 7.29 (1H, d, J~2.1 Hz), 7.34 (1H, d, J~8.1 Hz)

Ethyl-4-(2,2,4,4-tetramethyl-7-thiochromanyl) ethynyl-benzoate (Compound 3)

A solution of 390 mg (1.7 mmol) of 2,2,4,4 tetramethyl-7-ethynyl-thio chroman (Compound 38) and 552 mg (2.0 mmol) of ethyl 4-iodobenzoate in 3 ml of triethylamine was placed in a heavy walled glass tube and degassed for 0.25 hours under nitrogen. The mixture was treated with 18 mg (0.256 mmol) of bis (triphenylphosphine) palladium (II) chloride and 8 mg (0.042 mmol) of cuprous iodide under nitrogen and stirred for 5 minutes. The mixture was treated again with the same amounts of bis (triphenylphosphine) palladium II chloride and cuprous iodide, and the mixture was degassed again. The tube was then sealed and the reaction mixture was heated at 45° C. for 70 hours and then cooled to room temperature. The reaction mixture was filtered through celite and the solvent was removed under vacuum. The residue was purified by flash column chromatography (silica; 1%/Ethylacetate in hexane) to give the title compound as a white solid.

PMR (CDCl3): & 1.37–1.43 (15H, m), 1.96 (2H, s), 4.39 (2H, q, J~7.0 Hz), 7.26 (1H, dd, J~8.2 Hz, 1.8 Hz), 7.34 (1H, d, J~1.8 Hz), 7.37 (1H, d, J~8.2 Hz), 7.56 (2H, d, J ~8.0 Hz), 8.02 (2H, d, J~8.0 Hz).

3-Bromophenyl 3,3-dimethyl acrylate (Compound 39)

To an ice-cooled suspension of 4 g (100 mmol) of sodium hydride (60% in mineral oil) in 50 ml of dry THF was added dropwise a solution of 15.7 g (90.7 mmol) of 3-bromo phenol in 25 ml of dry THF. The mixture was stirred at 0 degrees C. for 0.5 hours and then treated with a solution of 10.65 g (90.0 mmol) of dimethyl acryloyl chloride in 30 ml of dry THF. The mixture was allowed to warm to room temperature and stirred for 24 hours. The reaction mixture was poured onto 200 ml of ice water containing 3 ml of glacial acetic acid. The mixture was extracted with 2×250 ml ether and the combined ether extracts were washed with 200 ml of water and 100 ml saturated NaCl solution and dried (MgSO4). The solvent was removed in vacuo and the residue purified by kugelrohr distillation to give the title compound as a clear oil.

PMR (CDCl$_3$): & 2.02 (3H, s), 2.28 (3H, s), 5.94 (1H, broad s), 7.06–7.12 (1H, m), 7.28 (1H, t, J~8.0 Hz), 7.34 (1H, t, J~2.0 Hz), 7.37–7.42 (1H, m).

3-Bromo-2-(1,1,3-Trimethyl-3-hydroxybutyl)phenol (Compound 41)

To a stirred, ice-cooled suspension of 21 g (158 mmol) of aluminum chloride in 200 ml of methylene chloride was added slowly a solution of 23.74 g (93.1 mmol) of 5-bromo-phenyl-3,3-dimethyl acrylate (Compound 39) in 100 ml of methylene chloride. The mixture was warmed to room temperature and stirred for 52 hours. The mixture was poured into a mixture of ice and brine and the organic layer was separated. The aqueous layer was extracted with 2×100 ml ether. The organic extracts were combined and washed with 2×250 ml of water and 50 ml of saturated NaCl solution and dried (MgSO$_4$). The solvent was removed in vacuo and the residue was partially purified by flash column chromatography, (silica; 5% ethyl acetate/hexane) to give impure 4,4-dimethyl-7-bromo-2-oxochroman (Compound 40) as a yellow oil which was used in the next step without further purification. To an ice-cooled solution of 10 g of this impure 4,4,dimethyl-7-bromo-2-oxochroman (Compound 40) in 200 ml of dry THF was added under argon 39.2 ml of 3.0M methyl magnesium chloride (117.6 mmol) in THF. The reaction mixture was allowed to warm to room temperature and stirred for 5 hours. The reaction mixture was then poured into ice water containing 2 ml of sulfuric acid and the organic layer was separated. The aqueous layer was extracted with 200 ml of ether. The organic extracts were combined and washed with 200 ml of water and 200 ml of brine and dried (MgSO$_4$). The solvent was removed in vacuo and the residue purified by flash column chromatography (silica; 10% ethylacetate/hexanes) to give the title compound as a pale yellow oil.

PMR (CDCl$_3$): & 0.98 (6H, s), 1.36 (6H, s), 2.15 (2H, s), 6.82 (1H, d, J~1.9 Hz), 6.86 (1H, dd, J~8.3 Hz, 1.9 Hz), 7.04 (1H, d, J~8.3 Hz).

2,2,4,4-tetramethyl-7-bromochroman (Compound 42)

A mixture of 5.42 (18.9 mmol) of 3-bromo-2(1,1,3 trimethyl-3-hydroxy-butyl) phenol (Compound 41) and 50 ml of 20 percent aqueous sulfuric acid was heated at reflux for 24 hours. The reaction mixture was cooled to room temperature and treated with 100 ml of ether. The organic layer was separated and the aqueous layer was extracted with 50 ml of ether. The ether extracts were combined and washed with 100 ml of water and 100 ml saturated NaCl solution and dried (MgSO$_4$). The solvent was removed in vacuo and the residue was purified by Kugelrohr distillation to give the impure title compound as a pale yellow oil.

PMR (CDCl$_3$): & 1.22 (6H, s), 1.24 (6H, s), 1.72 (2H, s), 6.87 (1H, d, J~2.0 Hz), 6.92 (1H, dd, J~8.3 Hz, 2.0 Hz), 7.02 (1H, d, J~8.3 Hz) .

2,2,4,4-Tetramethyl-7-trimethylsilylethynyl-chroman (Compound 43)

A solution of 2 g (7.4 mmol) of 2,2,4,4 tetramethyl-7-bromochroman (Compound 42) and 3.63 g (37.0 mmol) of trimethylsilylacetylene in 5 ml of triethylamine was placed in a heavy walled glass tube and degassed under nitrogen. The mixture was then treated, under nitrogen, with 130 mg (0.6826 mmol) of cuprous iodide and 260 mg (0.3704 mmol) of bis (triphenyl phosphine) palladium (II) chloride. The reaction mixture was degassed again and placed under nitrogen and the tube was sealed. The mixture was heated to 60 degrees C. for 24 hours and then cooled to room temperature and filtered through celite. The solvent was removed in vacuo and the residue purified by flash column chromatography (silica; 2% ethyl acetate/hexane) to give the title compound as a pale yellow solid.

PMR (CDCl$_3$): & 0.23 (9H, s), 1.32 (12H, s), 1.82 (2H, s), 6.92 (1H, d, J~1.6 Hz) 7.00 (1H, dd, J~8.6 Hz, 1.6 Hz) , 7.19 (1H, J~8.6 Hz)

2,2,4,4-tetramethyl-7-ethynyl chroman (Compound 44)

To a solution of 1.16 g (4.1 mmol) of 2,2,4,4-tetramethyl-7-trimethylsilylethynyl-chroman (Compound 43) in 3 ml of isopropanol was added 5 ml of ethanolic KOH solution. The reaction mixture was stirred at room temperature for 24 hours and the alcohol was then removed under vacuum. The residue was extracted with 2×10 ml of ether and the combined ether extracts were washed with 15 ml of water and 20 ml of saturated NaCl solution and then dried (MgSO$_4$). The solvent was removed in vacuo and the residue purified by Kugelrohr distillation to give the title compound as a white crystalline solid.

PMR (CDCl$_3$): & 1.33 (6H, s), 1.34 (6H, s), 1.83 (2H, s), 2.99 (1H, s), 6.94 (1H, d, J~1.7 Hz), 7.04 (1H, dd, J~8.0 Hz, 1.7 Hz), 7.21 (1H, d, J~8.0 Hz).

Ethyl-4-(2,2,4,4-tetramethyl-7-chromanyl)-ethynyl-benzoate (Compound 4)

A solution of 270 mg (1.26 mmol) of 2,2,4,4 tetramethyl-7-ethynyl chroman (Compound 44) and 420 mg (1.52 mmol) of ethyl 4-iodobenzoate in 4 ml of triethylamine was placed in a heavy walled glass tube and degassed under nitrogen for 15 minutes. The mixture was treated with 6 mg (0.0315 mmol) of cuprous iodide and 13 mg (0.0185 mmol) of bis(triphenylphosphine) palladium (II) chloride under nitrogen, and stirred for 5 minutes. The mixture was treated again with the same amounts of bis (triphenyl phosphine) palladium II chloride and cuprous iodide. The mixture was degassed again and the tube was sealed. The reaction mixture was heated to 45° for 70 hours and then cooled to room temperature. The reaction mixture was filtered through celite and the solvent was removed under vacuum. The residue was purified by flash column chromatography (silica; 1% ethyl acetate in hexanes) to give the title compound as a white solid.

PMR (CDCl$_3$): & 1.32 (6H, s), 1.33 (6H, s), 1.40 (3H, t, J ~7.2 Hz), 1.84 (2H, s), 4.38 (2H, d, J~7.2 Hz), 7.00 (1H, d, J~1.4 Hz), 7.09 (1H, dd, J~7.9 Hz, 1.4 Hz), 7.25 (1H, d, J ~7.9 Hz), 7.56 (2H, d, J~8.3 Hz), 8.02 (2H, J~8.3 Hz).

3-Bromophenyl-3-methyl-but-2-enylsulfide (Compound 45)

A solution of 25 g (132 mmol) of 3-bromothiophenol in 100 ml of acetone was heated to reflux and then treated with 5.56 g (139 mmol) of powdered NaOH. The mixture was refluxed for a further 0.5 hour. The refluxing mixture was then treated with a solution of 19.7 g (132 mmol) of 1-bromo-3-methyl-2-butene in 30 ml of acetone and refluxed for a further 1.5 hours. The mixture was cooled and then solvent was removed in-vacuo. The residue was extracted with ether and the ether extract was washed with dilute NaOH solution, water, and saturated NaCl solution and thereafter dried (CaCl$_2$). After evaporation of the solvent, the residue was purified by vacuum distillation to give the title compound as a white crystalline solid.

PMR (CDCl$_3$): & 1.61 (3H, s), 1.72 (3H, s), 3.52 (2H, d, J ~7.8 Hz), 5.27 (1H, t, J~7.8 Hz) 7.10 (1H, t, J~7.8 Hz), 7.21 (1H, dt, J~7.8 Hz, J~1.8 Hz), 7.27 (1H, dt, J~7.8 Hz, J~1.8 Hz), 7.44 (1H, t, J~1.8 Hz).

4,4,Dimethyl-7-trimethylsilylethynyl-Thiochroman (Compound 47)

To 3.63 g (14 mmol) of 3-bromophenyl-3-methyl-but-2-enyl sulfide (Compound 45) was added 15 g of a 1:10 P$_2$O$_5$, MeSO$_3$H mixture, and stirred at room temperature for 4 hours. The mixture was treated with cool water followed by boiling water. The mixture was stirred for 10 minutes and cooled to room temperature. The reaction mixture was then extracted with ether and the combined ether extracts were washed with water and then saturated NaCl solution and dried (CaCl$_2$). The solvent was removed in vacuo and the residue purified by Kugelrohr distillation (140 degrees C./0.2 mm) to give impure 4,4-dimethyl-7-bromo-thiochroman (Compound 46) as a pale yellow solid. This was used in the next step without further purification. A solution of 2.03 g of this impure 4,4 dimethyl-7-bromo thiochroman (Compound 46) in 2 ml of triethylamine was placed in a heavy-walled tube and degassed and then treated under argon with 3.8 g (38.9 mmol) of trimethylsilylacetylene a powdered mixture of 100 mg of bis (triphenylphosphine) palladium (II) chloride and 50 mg of cuprous iodide. The reaction mixture was degassed again, then placed under argon and the tube was sealed. The mixture was heated at 60° C. for 12 hours. The mixture was cooled to room temperature and then filtered through celite. The solvent was removed in vacuo and the residue purified by flash chromatography (silica; hexanes) to give the title compound as a yellow oil.

PMR (CDCl$_3$): & 0.22 (9H, s), 1.3 (6H, s), 1.91–1.98 (2H, t, J~6.0 Hz), 2.99–3.2 (2H, t, J~6.0 Hz) 7.09 (1H, dd, J~1.8, J~8.2 Hz) 7.20 (1H, d, J~1.8 Hz) 7.26 (1H, d, J~8.2 Hz).

Ethyl-4-(4,4-dimethyl-7-thiochromanyl)-ethynyl-benzoate (Compound 1)

To a solution of 1 g (3.6 mmol) of 4,4-dimethyl-7-trimethylsilylethynyl-thio-chroman (Compound 47) in 10 ml of isopropyl alcohol was added 5 ml of 1N KOH solution. The reaction mixture was stirred at room temperature for 18 hours and the isopropanol was then removed under vacuum. The residue was extracted with ether and the ether extracts were combined and washed with dilute HCl solution, water and saturated NaCl solution, and were thereafter dried (MgSO$_4$). The solvent was removed in vacuo to give impure 4-4-dimethyl-7-ethynyl-thiochroman (Compound 48) as a pale yellow oil. This mixture was used in the next step without further purification. A solution of 281 mg of this impure 4,4-dimethyl-7-ethynylthiochroman (Compound 48) and 384 mg (1.4 mmol) of ethyl 4-iodo-benzoate in 1 ml of triethylamine was placed in a heavy walled glass tube and degassed under nitrogen. The mixture was treated with 60 mg of cuprous iodide and 30 mg of bis (triphenyl phosphine) palladium (II) chloride. The reaction mixture was degassed again under nitrogen, and the tube was sealed. The reaction mixture was stirred at room temperature for 18 hours. The solvent was removed under high vacuum and the residue purified by flash column chromatography (silica; 3% EtOAC/hexane) to give the title compound as an off-white solid.

PMR (CDCl$_3$): & 1.32 (6H, s), 1.40 (3H, t, J~7.1 Hz), 1.92–1.99 (2H, m), 2.99–3.06 (2H, m), 4.38 (2H, q, J~7.1 Hz, 7.17 (1H, dd, J~8.2 Hz, 1.7 Hz), 7.28 (1H, d, J~1.7 Hz), 7.34 (1H, d, J~8.2 Hz), 7.55 (2H, d, J~8.5 Hz), 8.01 (2H, d, J~8.5 Hz).

4-[4-4-Dimethyl-7-thiochromanyl)-ethynyl] benzoic acid (Compound 2)

To 150 mg (0.428 mmol) of ethyl-4-(4,4-dimethyl-7-thiochromanyl-ethynyl-benzoate (Compound 1) was added 5 ml of ethanolic KOH solution and the reaction mixture was stirred at room temperature for 24 hours. The ethanol was removed in vacuo and the residue was taken up in 3 ml of water and 3 ml of ether. The layers were separated and the aqueous layer was washed with ether. The aqueous layer was acidified to Ph=2 with 1N HCl and was extracted with 2×20 ml of ether. The combined ether extracts were washed successively with water and saturated NaCl solution and then dried (MgSO$_4$). The solvent was removed in vacuo to give the title compound as a white solid.

PMR (CDCl$_3$): & 1.30 (6H, s), 1.91–1.97 (2H, m), 2.99–3.04 (2H, m), 7.14 (1H, dd, J~8.1 Hz, 1.7 Hz), 7.24 (1H, d, J~1.7 Hz), 7.32 (1H, d, J~8.1 Hz), 7.52 (2H, d, J~8.3 Hz), 7.99 (2H, d, J~8.3 Hz).

4-(2,2,4,4-Tetramethyl-7-thiochromanyl)-ethynyl-benzoic acid (Compound 49)

To 99 mg (0.262 mmol) of ethyl-4-(2,2,4,4-tetramethyl-7-thiochromanyl) ethynyl-benzoate (Compound 3) was added 5 ml of an ethanolic KOH solution. The reaction mixture was stirred at room temperature for 48 hours and the solvent was then removed in vacuo. The residue was taken up with water and ether and the layers were separated. The aqueous layer was acidified to Ph~2 with 1N HCl and extracted with ether. The ether layer was then washed with water and saturated sodium chloride and then dried (MgSo$_4$). The solvent was removed in vacuo to give the title compound as a white solid PMR (CDCl$_3$): & 1.40 (6H, s), 1.42 (6H, s), 1.98 (2H, s), 7.23–7.29 (2H, m), 7.43 (1H, d, J~8.6 Hz), 7.57 (2H, d, J~8.5 Hz), 8.01 (2H, d, J~8.5 Hz).

4- (2,2,4,4-tetramethyl-7-chromanyl)-ethynyl benzoic acid (Compound 50 )

To 207.2 mg (0.572 mmol) of ethyl-4-(2,2,4,4-tetramethyl-7-chromanyl) ethynyl-benzoate (Compound 4) was added 5 ml of ethanolic KOH solution. The reaction mixture was stirred at room temperature for 48 hours and the solvent was then removed in vacuo. The residue was taken up with water and ether and the layers were separated. The aqueous layer was acidified to Ph~2 with 1N HCl and extracted with ether. The ether layer was then washed with water and saturated sodium chloride and then dried (MgSO$_4$). The solvent was removed in vacuo to give the title compound as a pale yellow solid.

PMR (CDCl$_3$): & 1.37 (12H, s), 1.87 (2H, s), 6.95 (1H, d, J~1.6 Hz), 7.09 (1H, dd, J~8.0 Hz, 1.6 Hz), 7.30 (1H, d, J ~8.0 Hz), 7.57 (2H, d, J~8.3 Hz), 8.02 (2H, d, J~8.3 Hz).

What is claimed is:

1. A compound of the formula

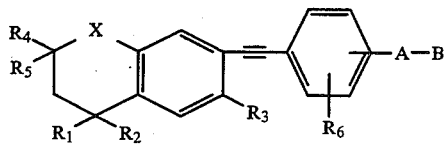

where X is S or O;

R₁, R₂, R₄ and R₅ independently are hydrogen or lower alkyl of 1 to 3 carbons, and R₃ is hydrogen or lower alkyl;

A is lower branched chain alkyl having 2 to 6 carbons, cycloalkyl having 3 to 6 carbons, alkenyl having 2 to 6 carbons and 1 or 2 double bonds, alkynyl having 2 to 6 carbons and 1 or 2 triple bonds, $(CH_2)_n$ and where n is an integer from 0–5;

R₆ is hydrogen, lower alkyl, lower alkenyl or lower cycloalkyl having 1 to 6 carbons, or halogen; and B is COOH or a pharmaceutically acceptable salt thereof, $COOR_8$, $COONR_9R_{10}$, where R₈ is an alkyl group of 1 to 10 carbons, or a cycloalkyl group of 5 to 10 carbons, or R₈ is phenyl or lower alkylphenyl, R₉ and R₁₀ independently are hydrogen, an alkyl group of 1 to 10 carbons, or a cycloalkyl group of 5 to 10 carbons, or phenyl or lower alkylphenyl.

2. A compound of claim 1 where X is S.

3. A compound of claim 2 where A is $(CH_2)_n$ and n is 0, 1, or 2.

4. A compound of claim 3 where R₄ is H and R₅ is lower alkyl.

5. A compound of claim 3 where R₄ is the same alkyl group as R₅.

6. A compound of claim 3 where R₄ is lower alkyl and R₅ is lower alkyl and R₄ and R₅ are different.

7. A compound of claim 3 where R₄ and R₅ are both hydrogen.

8. A compound of claim 1 where X is O.

9. A compound of claim 8 where A is $(CH_2)_n$ and n is 0, 1, or 2.

10. A compound of claim 9 where R₄ is H and R₅ is lower alkyl.

11. A compound of claim 9 where R₄ is lower alkyl and R₅ is lower alkyl and R₄ and R₅ are different.

12. A compound of claim 9 where R₄ is the same alkyl group as R₅.

13. A compound of claim 10 where R₄ and R₅ are both H.

14. A pharmaceutical composition comprising one or more compounds set forth in claim 1, the composition including a pharmaceutically acceptable excipient.

15. A compound of the formula

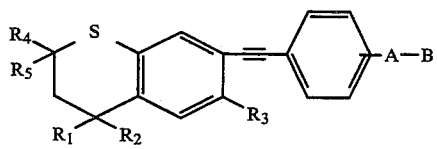

where R₁, R₂, R₄ and R₅ independently are hydrogen or lower alkyl of 1 to 3 carbons and R₃ is hydrogen or lower alkyl;

A is lower branched chain alkyl having 2 to 6 carbons, cycloalkyl having 3 to 6 carbons, alkenyl having 2 to 6 carbons and 1 or 2 double bonds, alkynyl having 2 to 6 carbons and 1 or 2 triple bonds, $(CH_2)_n$ where n is an integer between 0 to 5; and B is COOH or a pharmaceutically acceptable salt thereof, $COOR_8$, $COONR_9R_{10}$, where R₈ is an alkyl group of 1 to 10 carbons, or a cycloalkyl group of 5 to 10 carbons, or R₈ is phenyl or lower alkylphenyl, R₉ and R₁₀ independently are hydrogen, an alkyl group of 1 to 10 carbons, or a cycloalkyl group of 5 to 10 carbons, or phenyl or lower alkylphenyl.

16. A compound of claim 15 wherein A is $(CH_2)_n$ and n is 0.

17. A compound of claim 16 where R₁–R₅ are independently H or methyl.

18. A compound of claim 17 where B is $COOC_2H_5$.

19. The compound of claim 18 where R₃ is H and R₁, R₂, R₄ and R₅ are methyl.

20. The compound of claim 18 where R₁, R₂ are methyl and R₃, R₄ and R₅ are hydrogen.

21. A compound of claim 17 where B is COOH.

22. A compound of claim 21 where R₃ is H and R₁, R₂, R₄ and R₅ are methyl.

23. A compound of claim 21 where R₁ and R₂ are methyl and R₃, R₄ and R₅ are H.

24. The compound of claim 16 where B is COOH or a pharmaceutically acceptable salt thereof, R₁, R₂ are methyl, and R₃, R₄ and R₅ are hydrogen.

25. A compound of the formula

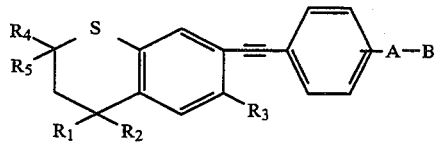

where R₁, R₂, R₄ and R₅ independently are hydrogen or lower alkyl of 1 to 3 carbons and R₃ is hydrogen or lower alkyl;

A is lower branched chain alkyl having 2 to 6 carbons, cycloalkyl having 3 to 6 carbons, alkenyl having 2 to 6 carbons and 1 or 2 double bonds, alkynyl having 2 to 6 carbons and 1 or 2 triple bonds, $(CH_2)_n$ where n is an integer between 0 to 5, and B is COOH or a pharmaceutically acceptable salt thereof, $COOR_8$, $COONR_9R_{10}$, where R₈ is an alkyl group of 1 to 10 carbons, or a cycloalkyl group of 5 to 10 carbons, or R₈ is phenyl or lower alkylphenyl, R₉ and R₁₀ independently are hydrogen, an alkyl group of 1 to 10 carbons, or a cycloalkyl group of 5 to 10 carbons, or phenyl or lower alkylphenyl.

26. A compound of claim 25 where A is $(CH_2)_n$ and n is 0.

27. A compound of claim 26 where B is $COOC_2H_5$.

28. The compound of claim 27 where R₃ is hydrogen, R₁, R₂, R₄ and R₅ are methyl.

29. A compound of claim 26 where B is COOH.

30. A compound of claim 29 where R₃ is hydrogen, R₁, R₂, R₄ and R₅ are methyl.

* * * * *

UNITED STATES PATENT AND TRADEMARK OFFICE
CERTIFICATE OF CORRECTION

PATENT NO. : 5,346,915
DATED : September 13, 1994
INVENTOR(S) : Roshantha A.S. Chandraratna It is certified that error appears in the above-indentified patent and that said Letters Patent is hereby corrected as shown below:

Title page, item [54] and col. 1, line 3, in the title, "RETINOLD-LIKE" should be --RETINOID-LIKE--;
Column 21, line 2, "nto" should be --into--;
Column 26, line 5, before "7.17", "Hz" should be --Hz)--;
Column 26, line 41, "Mgso4" should be --$MgSO_4$--.

Signed and Sealed this

Second Day of January, 1996

Attest:

BRUCE LEHMAN

*Attesting Officer*     Commissioner of Patents and Trademarks